(12) United States Patent
Kang

(10) Patent No.: US 10,806,883 B2
(45) Date of Patent: Oct. 20, 2020

(54) CATHETER GUIDE STRUCTURE

(71) Applicant: LMECA CO., LTD., Wonju-si, Gangwon-do (KR)

(72) Inventor: Jung-Kil Kang, Goyang-si (KR)

(73) Assignee: LMECA CO., LTD., Wonju-si, Gangwon-do (KR)

( * ) Notice: Subject to any disclaimer, the term of this patent is extended or adjusted under 35 U.S.C. 154(b) by 679 days.

(21) Appl. No.: 15/250,314

(22) Filed: Aug. 29, 2016

(65) Prior Publication Data
US 2017/0281890 A1 Oct. 5, 2017

(30) Foreign Application Priority Data
Mar. 29, 2016 (KR) .................. 10-2016-0037423

(51) Int. Cl.
*A61M 16/04* (2006.01)
*A61M 39/22* (2006.01)
(Continued)

(52) U.S. Cl.
CPC ........ *A61M 16/0463* (2013.01); *A61M 16/00* (2013.01); *A61M 16/0465* (2013.01); *A61M 16/0833* (2014.02); *A61M 16/105* (2013.01); *A61M 16/201* (2014.02); *A61M 39/10* (2013.01); *A61M 39/227* (2013.01);
(Continued)

(58) Field of Classification Search
CPC .. A61M 2202/0468; A61M 2202/0007; A61M 2202/0208; A61M 2202/0014; A61M 16/00; A61M 16/0463; A61M 16/0465; A61M 16/0833; A61M 16/105; A61M 16/201; A61M 2016/003;
(Continued)

(56) References Cited

U.S. PATENT DOCUMENTS

| 4,805,611 | A | * | 2/1989 | Hodgkins | .......... | A61N 16/0463 128/207.14 |
| 4,850,350 | A | | 7/1989 | Jackson | | |
| 5,354,267 | A | | 10/1994 | Niermann et al. | | |
| 2003/0047189 | A1 | * | 3/2003 | Kumar | ............. | A61M 16/0488 128/206.29 |

(Continued)

FOREIGN PATENT DOCUMENTS

| EP | 1994-898 A1 | 11/2008 |
| FR | 2884150 A1 | 10/2006 |

(Continued)

*Primary Examiner* — Annette Dixon
(74) *Attorney, Agent, or Firm* — Rabin & Berdo, P.C.

(57) ABSTRACT

A catheter guide structure is disclosed. Provided are a first guide module provided with an oxygen supply opening, a second guide module connected to the first guide module, and having an internal space that is opened only when the advancement of the catheter into the first guide module is necessary, and a third guide module connected to the second guide module to guide the advancement of the catheter into the first guide module. Accordingly, efficiency is ensured for the process of inserting a catheter in a respiratory system of a patient to suction foreign substances such as sputum present in the respiratory system of the patient assisted by the respirator and the process of removing the catheter such that nursing treatment for the patient can be provided with speed and efficiency. Further, according to the present disclosure, cleaning and sterilization inside and outside the catheter can be performed with ease.

1 Claim, 4 Drawing Sheets

(51) Int. Cl.
  *A61M 16/08* (2006.01)
  *A61M 16/20* (2006.01)
  *A61M 16/00* (2006.01)
  *A61M 39/10* (2006.01)
  *F16K 7/10* (2006.01)
  *A61M 16/10* (2006.01)

(52) U.S. Cl.
  CPC ......... *F16K 7/10* (2013.01); *A61M 2016/003* (2013.01); *A61M 2202/0208* (2013.01); *A61M 2202/0468* (2013.01); *A61M 2209/10* (2013.01)

(58) Field of Classification Search
  CPC .. A61M 2209/10; A61M 25/01; A61M 39/10; A61M 39/227; F16K 7/10
  See application file for complete search history.

(56) References Cited

U.S. PATENT DOCUMENTS

| | | | |
|---|---|---|---|
| 2007/0093749 A1 | 4/2007 | Spranger | |
| 2014/0338667 A1* | 11/2014 | Baczkowski | A61M 16/201 128/203.28 |
| 2015/0034077 A1* | 2/2015 | Kraft | A61M 11/06 128/200.23 |
| 2015/0314101 A1* | 11/2015 | Acker | A61M 16/06 128/203.14 |

FOREIGN PATENT DOCUMENTS

| | | |
|---|---|---|
| JP | S57-188249 A | 11/1982 |
| JP | 2013-236708 A | 11/2013 |
| WO | WO 00-24439 A1 | 5/2000 |

* cited by examiner

CATHETER GUIDE STRUCTURE

TECHNICAL FIELD

The present disclosure relates to a catheter guide structure, and more particularly, to a catheter guide structure that ensures efficiency of the process of inserting a catheter in a respiratory system of a patient to suction foreign substances such as sputum present in the respiratory system of the patient assisted by the respirator and the process of removing the catheter such that nursing treatment for the patient can be provided with speed and efficiency, and cleaning and sterilization inside and outside the catheter can also be performed with ease.

BACKGROUND ART

Medical suction equipment refers to an apparatus that suctions foreign substance for medical purpose during treatment at a hospital, by forcibly suctioning foreign substance such as blood, saliva, vomitus, secretion, and so on that are generated in a patient's body.

Generally, patients with reduced mobility are constantly assisted with a suction equipment such that a caregiver or a nurse at hospital or home can remove foreign substances from an airway or surgical site of the patient.

Meanwhile, when foreign substance such as sputum is generated in the respiratory system of a patient assisted with the respirator, a nurse inserts a catheter of the medical suction equipment into the respiratory system of the patient assisted with the respirator to remove the foreign substance.

In the procedure of suctioning foreign substance as described above, a nurse has to ensure that a passage for a catheter, which is separately provided in the respirator, is kept closed at normal circumstances, while he or she temporarily opens the catheter passage when it is necessary to suction foreign substance from the respiratory system. Conventionally, such closing and opening procedure of the catheter passage has to be performed by a medical attendance, and this can cause inefficiency in the procedure such that it is difficult to suction foreign substance necessary for the patient in a timely manner.

In addition, the difficulty of cleaning and maintenance of a conventional catheter of a medical suction equipment causes a technical limit that the catheter is usually disposed after used once.

DISCLOSURE OF INVENTION

Technical Problem

An object of the present disclosure is to solve the problems mentioned above, and accordingly, it is an object of the present disclosure to provide a catheter guide structure that ensures efficiency of the process of inserting a catheter in a respiratory system of a patient to suction foreign substances such as sputum present in the respiratory system of the patient assisted by the respirator and the process of removing the catheter such that nursing treatment for the patient can be provided with speed and efficiency, and cleaning and sterilization inside and outside the catheter can also be performed with ease.

Solution to Problem

In order to achieve the above and other objects of the present disclosure, provided is a catheter guide structure for guiding an advancement of a catheter into a respiratory system in which the catheter is provided on a medical suction equipment to remove a foreign substance from inside a respiratory system, in which the catheter guide structure may include a first guide module 100 provided with an oxygen supply opening 110, a second guide module 200 connected to the first guide module 100, and comprising an internal space that is opened only when the advancement of the catheter into the first guide module 100 is necessary, and a third guide module 300 connected to the second guide module 200 to guide the advancement of the catheter into the first guide module 100.

Preferably, the internal space provided in the second guide module 200 is filled with a balloon 285 that is inflated by an operation of a user.

Further, the third guide module 300 includes an inlet 350 on a side surface to introduce a saline solution into the catheter.

Advantageous effect

According to the present disclosure, efficiency is ensured for the process of inserting a catheter in a respiratory system of a patient to suction foreign substances such as sputum present in the respiratory system of the patient assisted by the respirator and the process of removing the respirator such that nursing treatment for the patient can be provided with speed and efficiency.

Further, according to the present disclosure, cleaning and sterilization inside and outside the catheter can be performed with ease.

MODE FOR THE INVENTION

Figure 1:
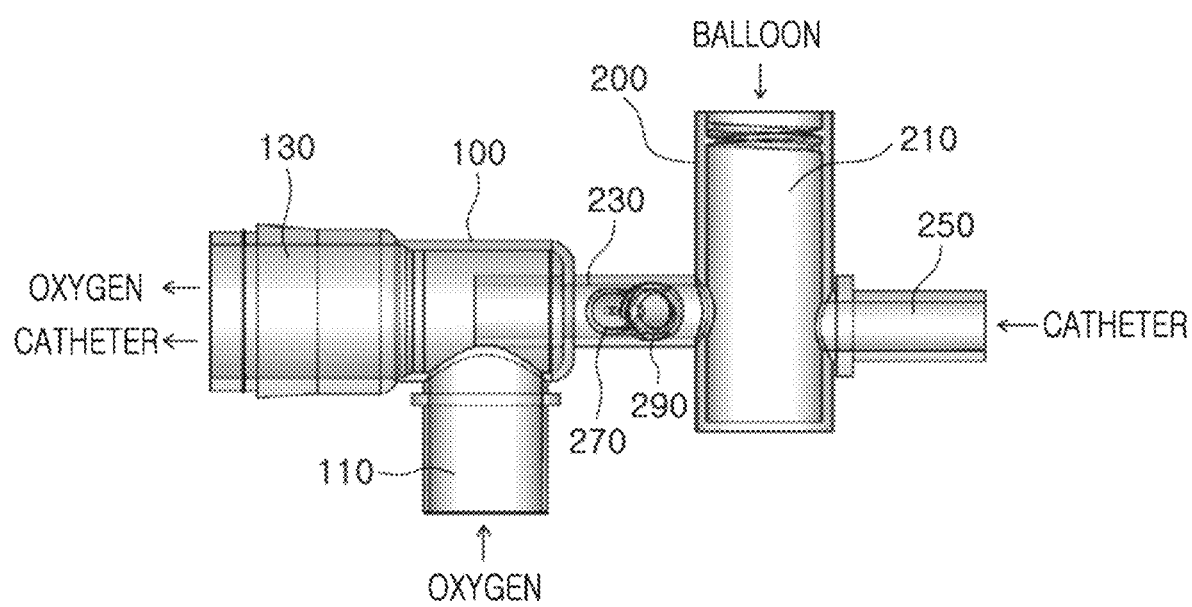
FIG. 1 is a side view illustrating a structure of a catheter guide structure according to an exemplary embodiment of the present disclosure.

Certain exemplary embodiments of the present inventive concept will be described in greater detail with reference to the accompanying drawings to enable those skilled in the art to work the present disclosure. It is to be noted that the same drawing reference numerals are used for the same elements even in different drawings. Further, in the following description, issues irrelevant with the description are not described as these may obscure the description.

Figure 2:
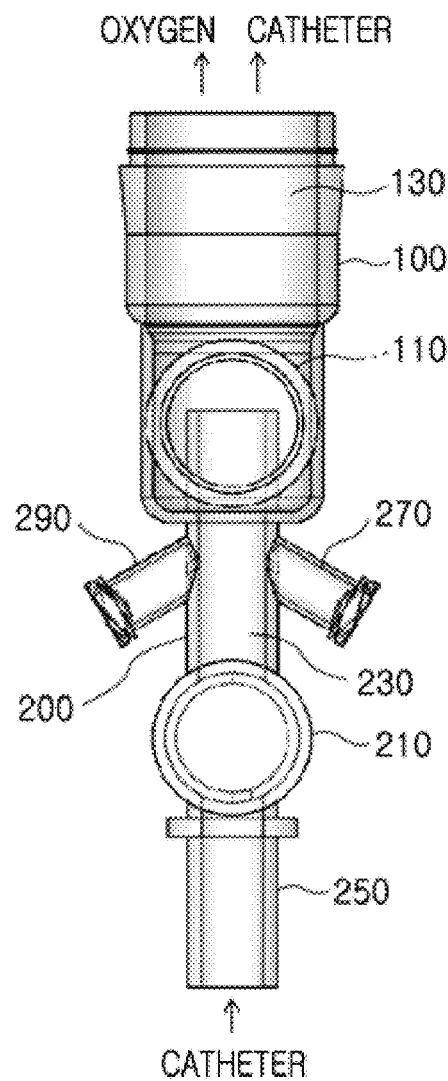
FIG. 2 is a top view illustrating a structure of a catheter guide structure according to an exemplary embodiment of the present disclosure.

FIG. 1 is a side view illustrating a structure of a catheter guide structure according to an exemplary embodiment of the present disclosure, and FIG. 2 is a top view illustrating a structure of a catheter guide structure according to an exemplary embodiment of the present disclosure.

According to the present disclosure, a catheter guide structure serves a function of guiding the advancement of a catheter that is a suction tube provided in a medical suction equipment to remove foreign substance such as sputum, and so on from inside the respiratory system.

Referring to FIGS. 1 and 2, the catheter guide structure according to an exemplary embodiment includes a first guide module 100, and a second guide module 200 connected to the first guide module 100.

First, the first guide module 100 includes a main body 130, and an oxygen supply opening 110 provided on a side surface of the main body 130. One end of the main body 130 is fixedly provided on a neck of a patient to supply oxygen to the patient through the neck, or advances the catheter into the respiratory system of the patient. The other end of the main body 130 is connected with the second guide module 200.

Meanwhile, a respirator is provided at the oxygen supply opening 110, and the oxygen fed through the oxygen supply opening 110 is supplied to the patient through the main body 130. Meanwhile, an air cleaning filter may be installed within the oxygen supply opening 110 to supply cleaner oxygen to the patient.

Moreover, when coupling the first guide module 100 and the second guide module 200, the first guide module 100 may preferably be made free to rotate such that a user is able to adjust the direction of the oxygen supply opening 110 according to a location of the respirator and the environment of the patient's bed.

The second guide module 200 includes an opening and closing portion 210, a connector 230, a coupler 250, a first port 270, and a second port 290. The connector 230 serves a function to connect the second guide module 200 to the first guide module 100, and the coupler 250 is coupled with the third guide module 300.

The opening and closing portion 210 is formed perpendicularly to the direction of the advancement of the catheter, between the connector 230 and the coupler 250. The interior space is opened only when it is necessary that the catheter entering from the third guide module 300 is advanced into the first guide module 100. Unless it is necessary to advance the catheter, the interior space is filled with an inflated balloon 285 to prevent a circumstance that the oxygen supplied through the oxygen supply opening 110 is leaked outside through the coupler 250 instead of being supplied to the patient.

Meanwhile, as illustrated in FIG. 2, the first port 270 and the second port 290 are formed on the side surface of the connector 230. A mass flow meter (MFM) sensor to measure the mass of the patient's expired gas is connected to the first port 270, while the second port 290 serves a function of maintaining humidity of the airway and trachea of the patient.

In order to maintain humidity in the airway and trachea, saline solution is supplied through the second port 290 and when necessary, oxygen is supplied to the airway of the patient through the second port 290.

Figure 3:
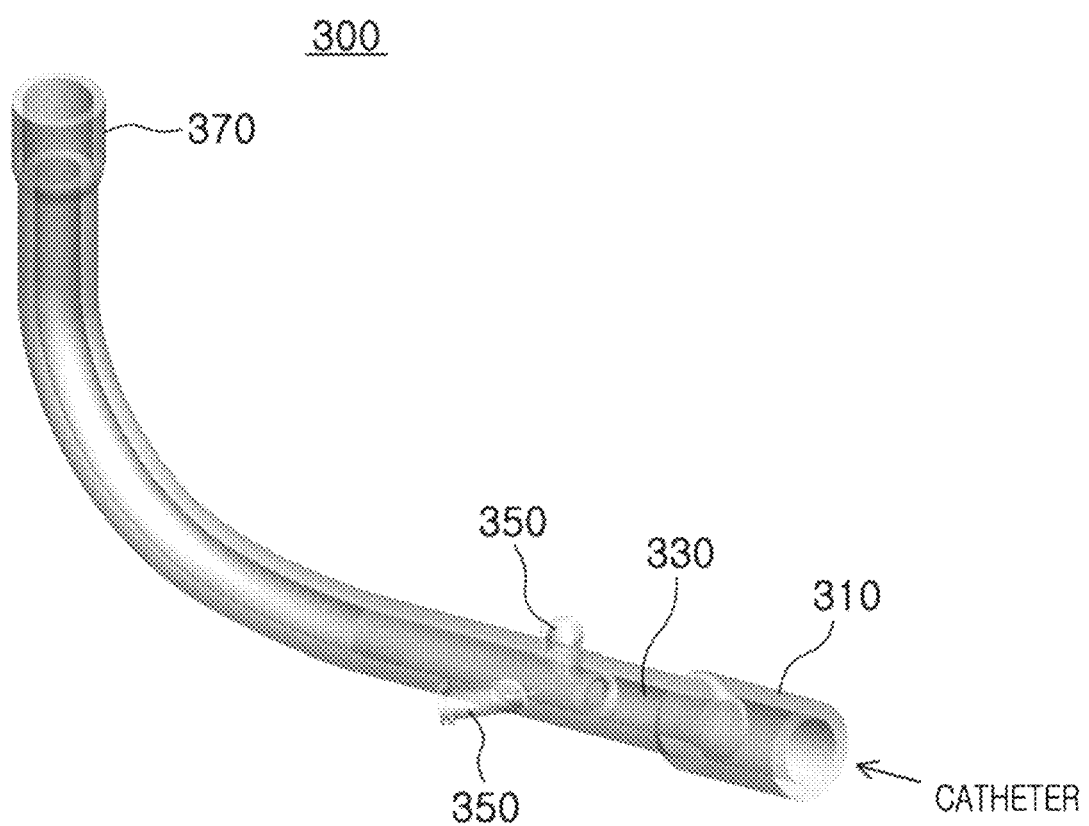
FIG. 3 illustrates a structure of a third guide module connected to the second guide module of FIGS. 1 and 2.

FIG. 3 illustrates a structure of a third guide module connected to the second guide module of FIGS. 1 and 2. Referring to FIG. 3, the third guide module 300 according to an exemplary embodiment includes a guide opening 310, a bottleneck portion 330, an inlet 350, and a fastener 370.

The guide opening 310 guides the insertion of the catheter, and when inserted through the guide opening 310, the catheter is advanced past the bottleneck portion 330 to the fastener 370.

Figure 4:
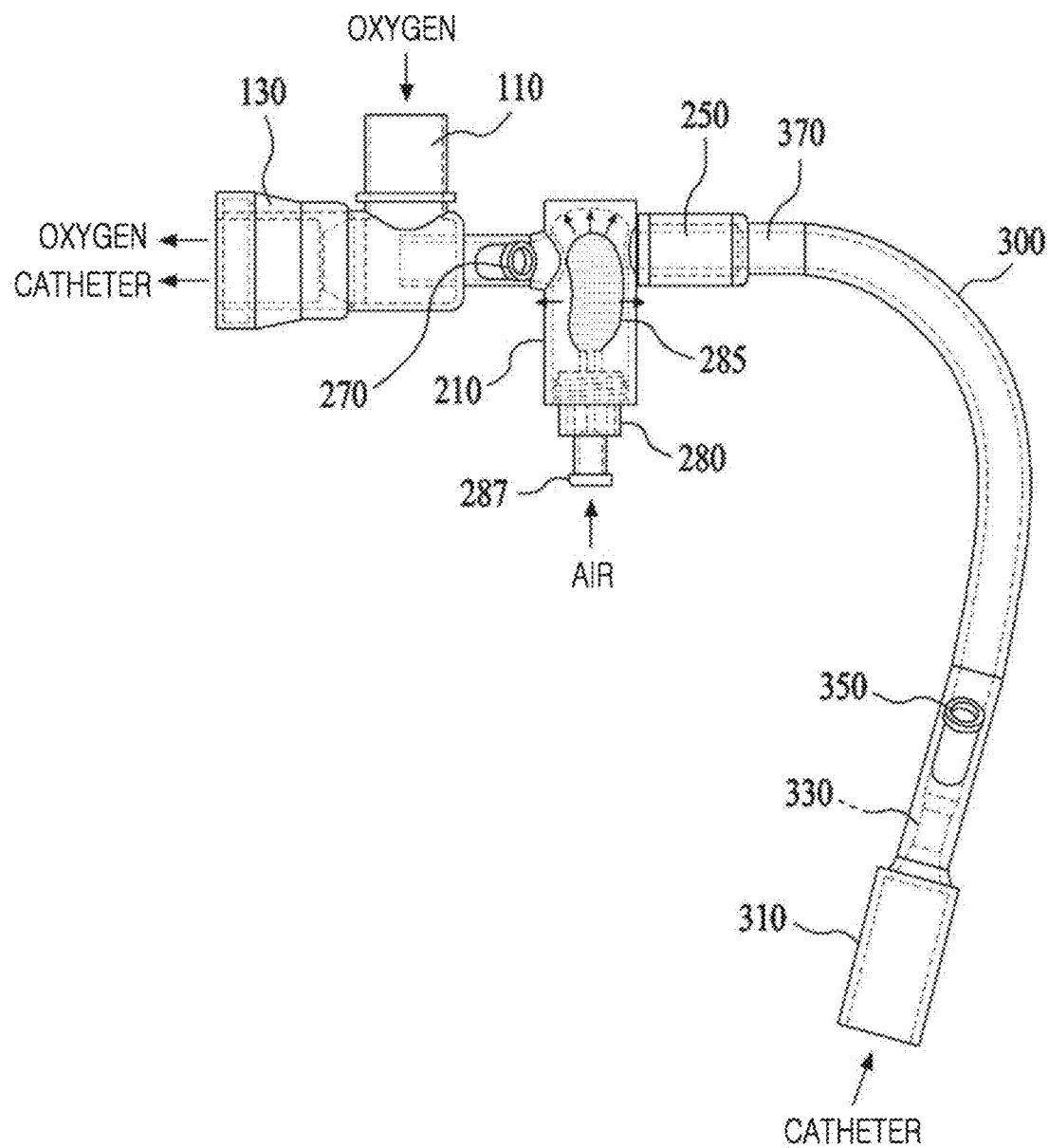
FIG. 4 is a view illustrating a first guide module, a second guide module, and a third guide module of a catheter guide structure being connected with one another, according to an exemplary embodiment of the present disclosure.

The fastener 370 is inserted into the coupler 250 of the second guide module 200 as illustrated in FIG. 4, and may preferably be free to rotate when inserted in the coupler 250.

In the example described above, the user is able to adjust the direction in which the third guide module 300 is installed, by adjusting the angle of rotation of the fastener 370 according to the location of the catheter supply apparatus and the environment of the bed. Since the catheter can be advanced into the second guide module 200 at a varying advancing angle, the user is able to adjust the angle of advancing the catheter to a direction where the pains of the patient can be minimized.

The bottleneck portion 330 forms a narrower-passage region in the moving passage of the catheter formed inside the third guide module 300. Specifically, it is preferable that the diameter of the moving passage of the catheter formed inside the bottleneck portion 330 almost corresponds to an outer diameter of the catheter within a range that does not cause frictional resistance on the outer surface of the catheter.

Meanwhile, the guide opening 310 is formed at a bottom end portion of the bottleneck region (i.e., lower end portion of the bottleneck region) of the moving passage that is formed by the bottleneck portion 330, while there is a pair of inlets 350 formed at a top end portion of the bottleneck region (i.e., upper end portion of the bottleneck region).

The user is able to supply saline solution or sterile water into the third guide module 300 through the pair of inlets 350 formed on the side surface of the third guide module 300, or more specifically, the user is able to clean or sterilize the inner walls of the catheter by positioning a suction end of the catheter at the upper end of the bottleneck region within the bottleneck portion 330 and supplying saline solution or sterile water through the inlets 350 such that the saline solution or the sterile water is introduced into the catheter.

Meanwhile, a fine spacing (approximately, 0.5 mm) may be present between the moving passage inside the bottleneck portion 330 and the outer surface of the catheter such that the saline solution or the sterile water supplied through the inlets 350 can also be supplied onto the outer surface of the catheter. As a result, the outer surface of the catheter can also be cleaned or sterilized.

According to an exemplary embodiment of the present disclosure, an expansion region (not illustrated), where the moving passage expands again, may be formed in the middle of the bottleneck region inside the bottleneck portion 330 such that the outer surface of the catheter can be submerged under the saline solution or the sterile water for a predetermined time (e.g., approximately 3 minutes). As a result, the efficiency of cleaning or sterilization of the outer surface of the catheter can be further increased.

Meanwhile, after a predetermined submerge time elapses, the saline solution or the sterile water, which are staying in the expansion region inside the bottleneck portion 330, may preferably be discharged out through the guide opening 310 with a suction equipment.

In addition, as the catheter is retreated backward from the forward insertion in the respiratory system, the foreign substance attached onto the outer surface of the catheter can be detached by a projection formed on the upper end of the bottleneck region and such detached foreign substance from the outer surface of the catheter can be discharged out through the guide opening 310 with the suction equipment.

As described above, according to the present disclosure, internal and external cleaning and sterilizing the catheter of the medical suction equipment can be facilitated.

FIG. 4 is a view illustrating the first guide module 100, the second guide module 200, and the third guide module 300 of a catheter guide structure being connected with one another, according to an exemplary embodiment of the present disclosure.

Referring to FIG. 4, the balloon 285 is installed at one end of the opening and closing portion 210 provided in the second guide module 200, and an opening and closing module 280 having an air introducing opening 287 is inserted into the other end.

Meanwhile, when it is unnecessary to remove foreign substance such as sputum from the respiratory system of the patient, the catheter does not have to be introduced into the first guide module 100. Accordingly, the controller (not illustrated) introduces air into the balloon 285 with an air compressor (not illustrated) connected to the air introducing opening 287 to inflate the balloon 285 installed in the interior space of the opening and closing portion 210 to accordingly fill the interior space. Accordingly, all the connecting passages between the opening and closing portion 210 and the coupler 250 and between the opening and closing portion 210 and the connector 230 are closed.

Since the interior space of the opening and closing portion 210 is closed as described above, when the oxygen is supplied through the oxygen supply opening 110 into the first guide module 100, loss of the oxygen to outside through the second guide module 200 and the third guide module 300 can be prevented. Furthermore, the contaminant such as sputum and so on that is suctioned into the catheter connected to the third guide module 300 can be prevented from contacting the patient through the first guide module 100, and possible contamination of the catheter connected to the third guide module 300 due to breath of the patient can also be prevented.

Meanwhile, when it is necessary to remove foreign substance such as sputum and so on from the respiratory system of the patient, the catheter is introduced into the first guide module 100. In this case, the controller (not illustrated) de-couples the air introducing opening 287 from the air compressor (not illustrated) and discharges air from the balloon. Accordingly, with the deflation of the balloon 285 installed in the internal space of the opening and closing portion 210, both the connecting passage between the opening and closing portion 210 and the coupler 250, and the connecting passage between the opening and closing portion 210 and the connector 230 are open.

With the opening of the internal space of the opening and closing portion 210 as described above, the catheter advancing through the third guide module 300 can be moved through the interiors of the second guide module 200 and the first guide module 100, to be entered into the respiratory system of the patient.

According to the exemplary embodiments described above, for inserting a catheter into a respiratory system of a patient assisted with a respirator to thus suction foreign substance such as sputum and so on present in the respiratory system, the process of opening the internal space of the opening and closing portion 210, and the process of closing the internal space of the opening and closing portion 210 after the removal of the catheter, can be performed automatically with the opening and closing module 280. As a result, fast and efficient nurse treatment for the patient can be provided.

Meanwhile, when the catheter is entered into the second guide module 200, the catheter is moved from the coupler 250 and through the opening and closing portion 210, and then entered into the first guide module 100 through the connector 230. In this process, i.e., in the process of entering the connector 230, the catheter moving into the connector 230 can preferably be prevented from being interfered with a protrusion at a border between the connector 230 and the opening and closing portion 230, by forming the coupler 250 at a vertical height greater than the vertical height of the connector 230 (by approximately 1 cm, for example), as illustrated in FIG. 4.

Meanwhile, in various exemplary embodiments, the function of the opening and closing module 280 implemented in a form of the balloon 285 may be replaced with a selective opening and closing function of a solenoid valve, a selective opening and closing function of an air curtain, a selective opening and closing function by an elastic returning force of an elastic structure such as a spring, and so on.

The terms are used herein only to describe certain exemplary embodiments, and these do not limit the present disclosure. A singular expression, unless otherwise specified in context, encompasses a plural expression. It is to be understood that the term such as "comprise" or "have" as used herein is to designate a presence of a characteristic, number, step, operation, element, component, or a combination of these, and not to foreclose a presence or possibility of adding one or more of other characteristics, numbers, steps, operations, elements, components or a combination of these.

The foregoing exemplary embodiments and advantages are merely exemplary and are not to be construed as limiting the exemplary embodiments. The present teaching can be readily applied to other types of apparatuses. Also, the description of the exemplary embodiments of the present inventive concept is intended to be illustrative, and not to limit the scope of the claims.

DESCRIPTION OF THE REFERENCE NUMERALS

100: first guide module
110: oxygen introducing opening
130: main body
200: second guide module
210: opening and closing portion
230: connector
250: coupler
270: first port
280: opening and closing module
285: balloon
287: air introducing opening
290: second port
300: third guide module
310: guide opening
330: bottleneck portion
350: inlet
370: fastener

What is claimed is:

1. A catheter guide structure for guiding an advancement of a catheter into a respiratory system, wherein the catheter is provided on medical suction equipment to remove a foreign substance from inside a respiratory system, the catheter guide structure comprising:

a first guide module provided with an oxygen supply opening;

a second guide module connected to the first guide module, and comprising an opening and closing portion having an internal space and an inflatable and deflatable balloon;

a connector to connect the second guide module to the first guide module;

a first port formed on a side surface of the connector, the first port to connect to a mass flow meter for measuring an expired gas, and a second port formed on the side surface of the connector, the second port to maintain humidity in a patient airway;
a third guide module connected to the second guide module to guide the advancement of the catheter into the first guide module; and
a coupler to couple the second guide module with the third guide module; wherein:
if the balloon is deflated, the internal space is not filled by the balloon and a connecting passage between the opening and closing portion and the coupler and between the opening and closing portion and the connector is open, and
if the balloon is inflated, the internal space is filled by the balloon and the connecting passage between the opening and closing portion and the coupler and between the opening and closing portion and the connector is closed;
the third guide module includes
  a bottleneck portion,
  a guide opening formed at a bottom end portion of the bottleneck portion,
  a pair of inlets formed at a side surface of the bottleneck portion, and
  a fastener formed at a top end portion of the bottleneck portion;
the fastener is insertable into the coupler and freely rotatable in the coupler to adjust an angle of advancement of the catheter into the second guide module;
the bottleneck portion has a moving passage corresponding to an outer surface of the catheter, the moving passage providing a spacing of approximately 0.5 mm between the moving passage and the outer surface of the catheter for introduction of a cleaning solution into the spacing via the pair of inlets, the cleaning solution being dischargeable from the guide opening;
a first inlet of the pair of inlets is offset from a second inlet of the pair of inlets in a circumferential direction on the side surface of the bottleneck portion; and
the coupler has a greater diameter than a diameter of the connector and is coupled to a first side of the second guide module at a greater height, in a side view, than a height at which the connector is coupled to a second side of the second guide module opposite the first side of the second guide module.

* * * * *